United States Patent [19]

Gray

[11] Patent Number: 4,851,007
[45] Date of Patent: Jul. 25, 1989

[54] FEMORAL COMPONENT FOR A HIP PROSTHESIS

[76] Inventor: Frank B. Gray, 5104 Lyons View Dr., Knoxville, Tenn. 37919

[21] Appl. No.: 169,960

[22] Filed: Mar. 18, 1988

[51] Int. Cl.⁴ .............................................. A61F 2/32
[52] U.S. Cl. ........................................ 623/23; 623/18
[58] Field of Search ...................... 623/16, 18, 20, 22, 623/23

[56] References Cited

U.S. PATENT DOCUMENTS

| | | | |
|---|---|---|---|
| 3,906,550 | 9/1975 | Rostoker et al. | 623/22 |
| 4,676,797 | 6/1987 | Anapliotis | 623/18 |
| 4,714,471 | 12/1987 | Grundei | 623/20 |

FOREIGN PATENT DOCUMENTS 0000549 2/1979 European Pat. Off. .............. 623/18

*Primary Examiner*—Richard J. Apley
*Assistant Examiner*—David J. Isabella
*Attorney, Agent, or Firm*—Pitts & Brittian

[57] ABSTRACT

A femoral component (10) for a hip prosthesis. The femoral component (10) comprises a femoral stem (18) including a proximal stem portion (24) for being implanted in the proximal portion of a femur and a distal stem portion (28) for being closely received in the medullary canal of the femur. The distal stem portion (28) is releasably secured to the lower end (32) of the proximal stem portion (24) such that the proximal and distal stem portions (24 and 28) can be independently sized to accommodate a specific femur configuration. The femoral component (10) further comprises a neck portion (20) and a head portion (22), the head portion (22) being releasably secured to the outboard end (52) of the neck portion (20). In the preferred embodiment, the proximal stem portion is held in place in the proximal femur through the use of a porous surface portion (42) which receives bone ingrowth from the femur.

10 Claims, 5 Drawing Sheets

FEMORAL COMPONENT FOR A HIP PROSTHESIS

TECHNICAL FIELD

This invention relates to an improved femoral component for a hip prosthesis. In this particular invention, the femoral component comprises a stem, including releasably joined proximal and distal stem portions, a neck portion and a head portion.

BACKGROUND ART

Hip prostheses for replacement of damaged or diseased human hips have long been known in the art. Such prosthetic devices generally comprise an acetabular component providing an artificial acetabulum, a femoral component including a femoral stem for implantation in the femur and a neck portion carrying a head for being rotatably received in the artificial acetabulum. Examples of such devices are disclosed in U.S. Pat. Nos. 4,365,358 and 4,514,865. Generally, the femoral stem of such devices integrally comprises a proximal portion for implantation in the proximal femur and a distal portion which is closely received in the medullary canal so as to extend into the diaphysis or shaft of the femur. Whereas such femoral components are offered in various sizes, difficulty can still be encountered in achieving a proper seating of the femoral stem in the femur. In this regard, where a femoral component is selected having a proximal portion appropriately sized for the proximal femur, the distal stem may not be of proper cross-sectional diameter for being closely received in the portion of the medullary canal into which it is to be implanted. For example, if the distal portion is too small, the stability of the implant can be undermined, and post surgical pain in the location of the distal stem can result. Accordingly, the femoral components presently known in the art are not interchangeably adaptable to various femur configurations.

Also known in the art is the use of femoral stems having porous exterior surface portions which receive bone ingrowth from the femur and thereby are secured in the femur. Whereas bone ingrowth is one of the preferred means of securing such femoral implants, femoral stems so implanted are very difficult to remove should replacement of the prosthesis be required. The general removal procedure involves the use of an osteotome to chisel the bone away from the porous surface and then the extraction of the femoral stem from the femur. However, this is a difficult procedure which can be highly destructive of the bone tissue of the proximal femur.

Therefore, it is an object of the present invention to provide an improved femoral component for a hip prosthesis.

It is another object of the present invention to provide an improved femoral component including a femoral stem having a proximal portion which releasably engages a cooperating distal portion such that the proximal and distal portions of the stem can be independently sized.

A further object of the present invention is to provide an improved femoral component which can feature a porous surface portion for being secured by bone ingrowth from the femur, yet is more easily removed for replacement.

Yet another object of the present invention is to provide an inventory of components which are inexpensive to manufacture and easy to implant.

DISCLOSURE OF THE INVENTION

Other objects and advantages will be accomplished by the present invention which provides a femoral component for a hip prosthesis utilized to replace a damaged or diseased human hip. The femoral component comprises a stem including a proximal stem portion for being implanted in the proximal femur and a distal stem portion for being closely received in the more distal medullary canal of the femur. The distal stem portion is releasably secured to the lower end of the proximal stem portion, rather than integrally formed with the proximal stem portion, such that the proximal and distal stem portions can be independently sized to accommodate a specific femoral configuration. In the preferred embodiment, the proximal stem portion is held in place in the proximal femur through the use of a porous surface portion provided on the peripheral surface of the proximal stem portion which receives bone ingrowth from the femur. The femoral component further comprises a neck portion which carries a head portion at its outboard end. In one embodiment, the proximal stem portion is provided with a resealable proximal sleeve, the sleeve defining the peripheral surface which secures the stem to the femur. If removal of the femoral component is desired, the proximal stem portion is removable from the sleeve to give access to the interior of the sleeve to facilitate removal of the distal stem portion from the femur.

BRIEF DESCRIPTION OF THE DRAWINGS

The above-mentioned features of the present invention will become more clearly understood from the following detailed description of the invention read together with the drawings in which.

BEST MODE FOR CARRYING OUT THE INVENTION

A femoral component incorporating various features of the present invention is illustrated generally at 10 in the figures. The femoral component 10 is used in conjunction with an acetabular component 12 to provide a total hip prosthesis for replacing a damaged or diseased human hip. More specifically, the acetabular component 12 is implanted in the innominate bone (not shown) and defines an artificial acetabulum 14 which serves to replace the natural acetabulum of the hip. Cooperatively, the femoral component 10 of the present invention is implanted in the femur 16 to replace the natural femoral neck and head.

Figure 1:
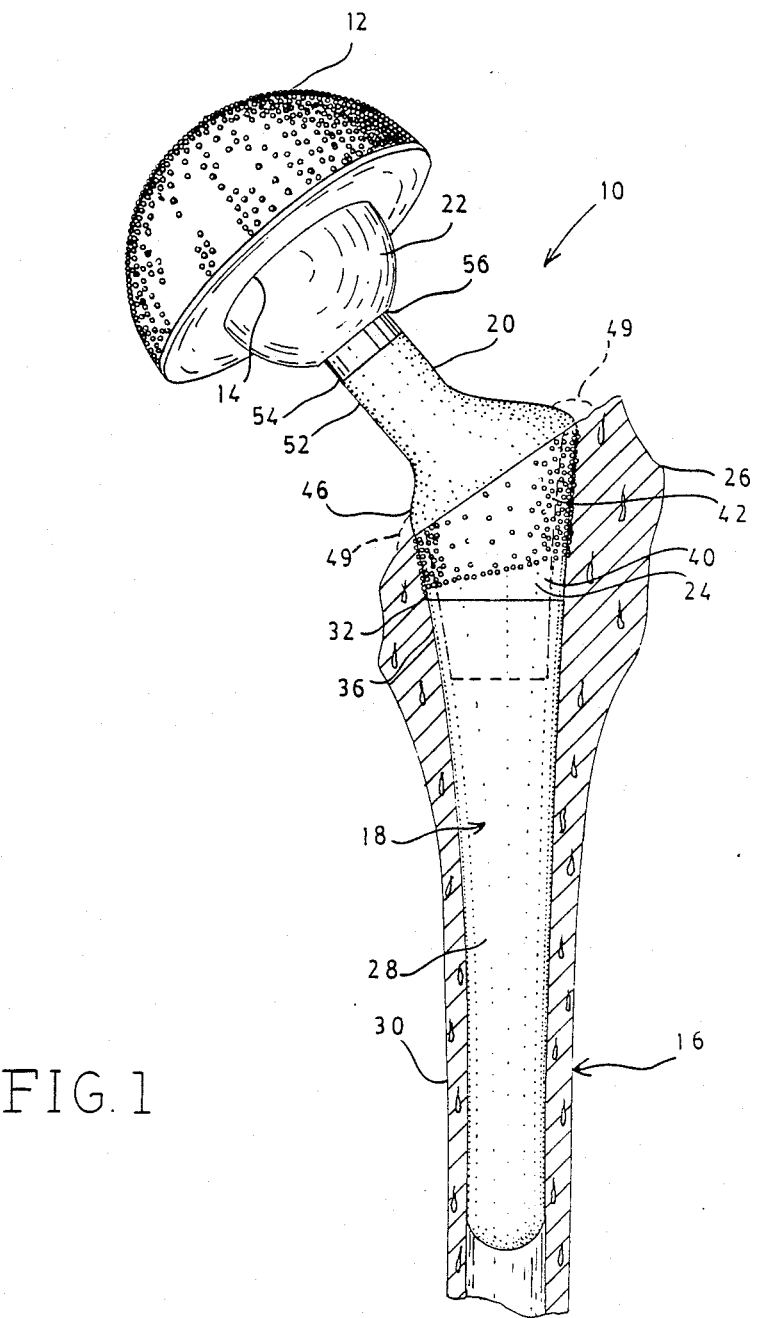
FIG. 1 illustrates a side elevation view of a femoral component of the present invention as implanted in a human femur.
Figure 2:
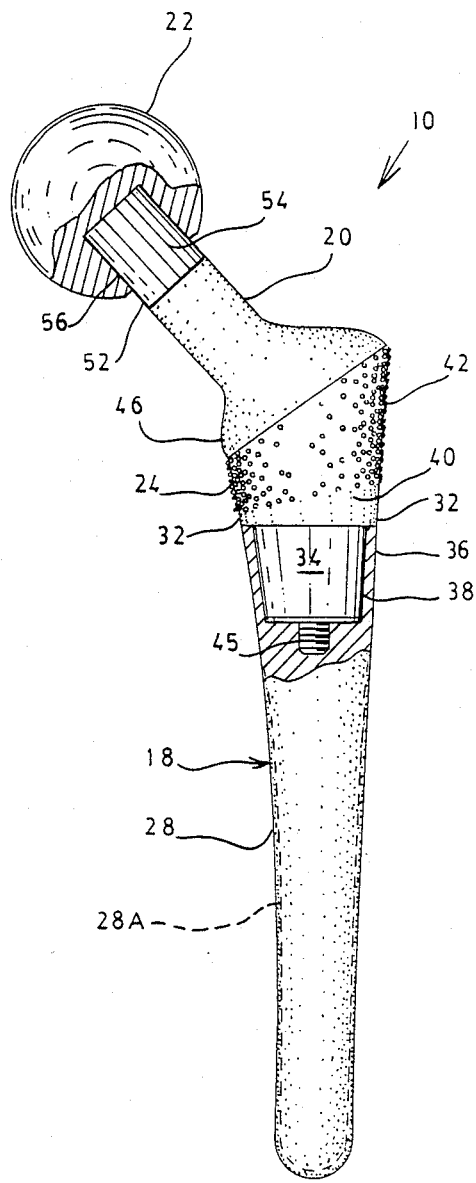
FIG. 2 illustrates a side elevation view, partially in section, of a femoral component of the present invention.

As illustrated in FIGS. 1 and 2, the femoral component 10 comprises a stem 18 for being implanted in the femur 16, a neck portion 20, and a head portion 22 for being rotatably received in the acetabulum 14. The stem 18 includes a proximal stem portion 24 which is received in the proximal femur 26 upon implantation and a distal stem portion 28 which is closely received in the medullary canal 30 so as to extend into the diaphysis of the femur 16. In the preferred embodiment, the upper end 36 of the distal stem portion 28 releasably engages the lower end 32 of the proximal stem portion 24. Whereas, various engaging means can be utilized for releasably joining the proximal and distal stem portions 24 and 28, in one preferred embodiment (see FIG. 2) the proximal stem portion 24 defines a lower end portion 32 which carries a protruding member 34, and the upper end portion 36 of the distal stem portion 28 defines a receptor 38 for closely receiving the protruding member 34. It will be noted that in the preferred embodiment, the protruding member 34 defines a morse cone and the receptor 38 defines tapered sidewalls for closely receiving the cone 34. Accordingly, the force-fit insertion of the cone 34 in the receptor 38 serves to releasably secure the stem portions 24 and 28 together. Further, it will be appreciated by those skilled in the art that the protruding member 34 can be provided on the upper end portion 36 of the distal stem portion 28, and the receptor 38 can be provided in the proximal stem portion 24 to effect the releasable engaging of the proximal distal stem portions if desired. This alternate construction will be discussed in detail below with respect to FIGS. 5A and 5B.

By providing for the releasable joining of the proximal and distal stem portions 24 and 28, the present invention, unlike conventional femoral components, allows the proximal and distal stem portions to be independently sized such that the stem 18 will be closely received by the femur 16 along the entire length of the stem. For example, as illustrated by the broken lines 28A, a distal stem having a smaller cross-sectional diameter than the portion 28 can be utilized with the proximal stem portion 24. In this regard, the implanting surgeon can preselect a proximal stem portion 24 of appropriate size for the specific femur into which it is to be implanted, and can preselect a distal stem portion 28 having the appropriate cross-sectional diameter for being closely received in the medullary canal of that particular femur.

As best illustrated in FIG. 1, the proximal stem portion 24 has a peripheral surface 40 defining a beaded or porous surface portion 42. It will be appreciated by those skilled in the art that post-implant bone ingrowth into the porous surface 42 serves to secure or fix the proximal stem portion 24 in position in the proximal femur 26. Of course, it will be understood that although the porous surface portion 42 represents the preferred means for securing the stem 18 in place, if desired, the porous surface portion 42 can be omitted and other suitable securing means, such as an adhesive or cement can be utilized to secure the stem 18 in position.

As indicated above, the head portion 22 replaces the natural femoral head, and preferably, the head portion 22 is releasably secured on the outboard end 52 of the neck portion 20. To accomplish the releasable securing of the head portion 22 to the neck portion 20, the outboard end 52 of the neck portion 20 defines a morse cone 54 and the head portion 22 is provided with a receptor 56 defining tapered sidewalls for closely receiving the cone 54. Accordingly, the force-fit insertion of the cone 54 into the receptor 56 accomplishes the releasable securing of the head portion 22 on the neck portion 20. Of course, it will be appreciated that such releasable securing means is simply one preferred means for securing the head portion 22 to the neck portion 20, and other securing means can be utilized.

With respect to the neck portion 20, it will be noted, as illustrated in FIG. 1, that the lower portion 46 of the neck portion 20 can be provided with a shoulder portion 49 which extends beyond the periphery of the proximal stem portion 24. It will be recognized that this shoulder portion 49 engages the proximal femur 26 thereby further stabilizing and supporting the neck portion 20.

Figure 3:
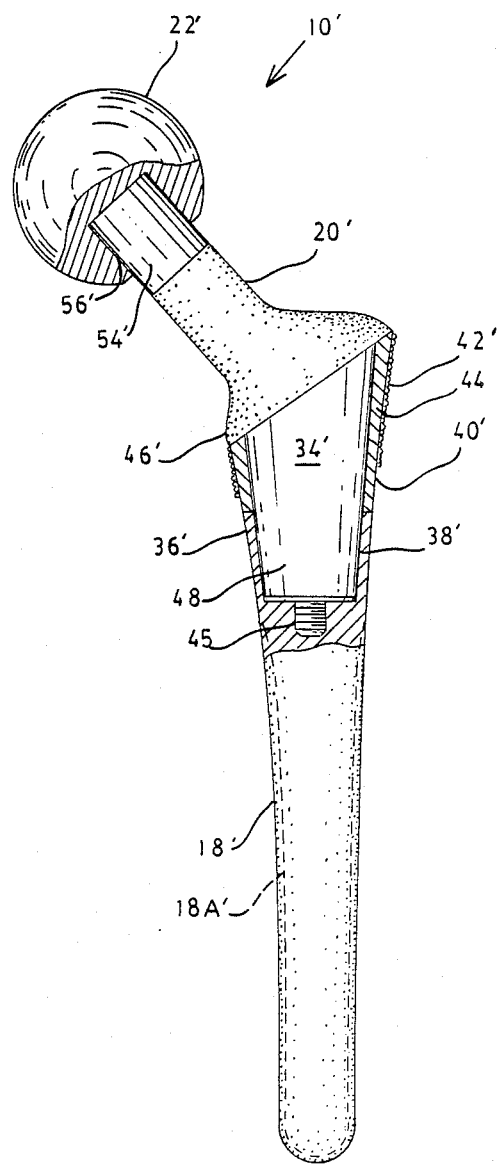
FIG. 3 illustrates a side elevation view, partially in section, of an alternate embodiment of a femoral component of the present invention.

In FIG. 3, an alternate embodiment of the femoral component of the present invention is illustrated at 10′. In this embodiment, the proximal stem portion 24′ comprises the protruding member 34′, preferably defining a morse cone, and interior walls, for being closely received by the protruding member 34′. More specifically, the protruding member 34′ extends downwardly from the lower portion 46′ of the neck portion 20′ and the sleeve 44 is closely received by the upper portion of the member 34′. The exterior of the sleeve defines the peripheral surface 40′ of the proximal stem portion 24′ and, accordingly, is provided with a porous surface portion 42′. When the sleeve member 44 is in position on the protruding member 34′, the free end portion 48 of the member 34′ extends beyond the sleeve 44 such that the free end portion can be force-fitted into the receptor 38′ of the distal stem 28′.

Figure 4A:
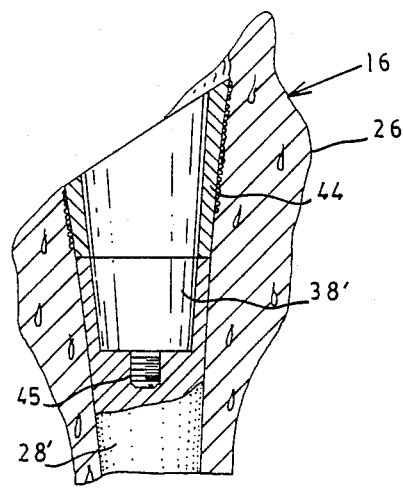
FIGS. 4A and 4B illustrate partial side elevations, partially in section, of the stem portion of a femoral component of the present invention.
Figure 4B:
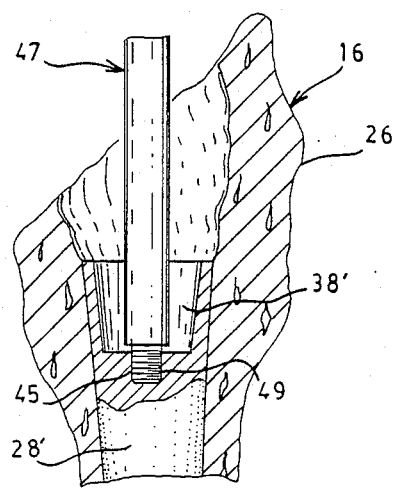

It will be recognized that, as with the component 10 of FIGS. 1 and 2, the femoral component allows the proximal and distal stem portions to be independently sized. However, the construction of the component 10′ also facilitates interchangeability of the neck portions 20′ and the total removal of the stem 18′ when removal is required after implantation. In this regard, because the protruding member 34′ is releasably force-fitted into the sleeve 44 and the receptor 38′, the member 34′ can be removed from the sleeve 44 and the receptor 38′ by applying upward force on the neck portion 20′, with a sharp rap from a suitable tool sometimes being necessary to initially dislodge the member 34′. With the neck portion 20′ and the member 34′ removed, only the sleeve 44 and the distal stem portion 28′ remain implanted as illustrated in FIG. 4A. Where a change of neck portions 20′ is desired, the new neck portion 20′ is secured in place by inserting the protruding member 34′ depending therefrom into the sleeve 44 and receptor 38′. Where removal of the entire component 10′ is desired, removal of the protruding member 34′ provides access to the interior of the sleeve 44 such that metal cutting tools can be used to cut away that portion of the sleeve which is secured by bone ingrowth or by other securing means. As illustrated in FIG. 4B, after the sleeve 44 has been removed, only the distal stem portion 28′ remains implanted. In order to facilitate the removal of the distal stem portion 28′, the stem portion 28′ can be provided with a further receptor 45 located in the bottom surface of the receptor 38′. As illustrated, the further receptor 45 is threadably receptive of the threaded end portion 49 of an extracting tool 47 (only a portion of which is shown) such that the extracting tool 47 can be used to pull the distal stem portion 28' from the femur.

Figure 5A:
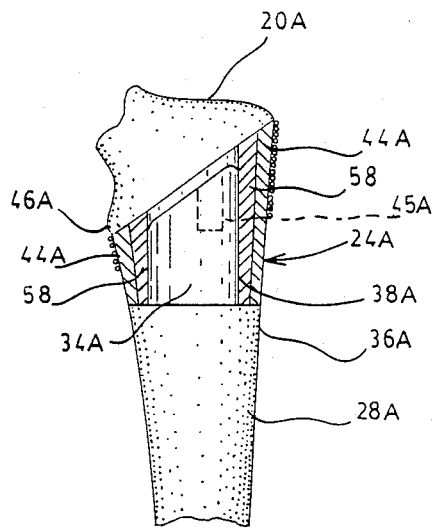
FIG. 5A illustrates a partial side elevation view, partially in section, of an alternate embodiment of a femoral component of the present invention.
Figure 5B:
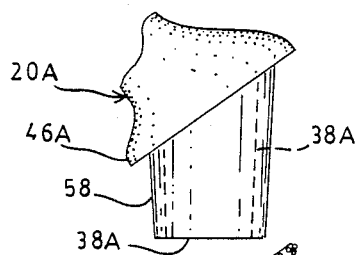
FIG. 5B illustrates a partial exploded side elevation view of an alternate embodiment of a femoral component of the present invention.
Figure 5B:
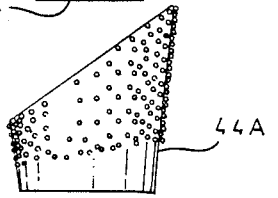
Figure 5B:
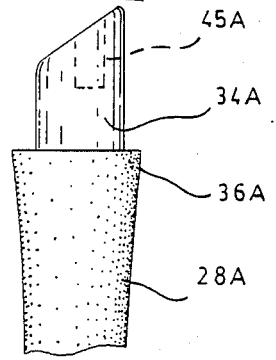

As indicated above, the protruding member 34, 34' can be provided on the upper end portion 36, 36' of the distal stem portion 28, 28', and the receptor 38 can be provided in the proximal stem portion 24, 24' in order to releasably secure the distal and proximal stem portions. An example of such construction is illustrated in FIGS. 5A and 5B. In this embodiment, the proximal stem portion 24A includes an inner sleeve 58 which extends downwardly from the lower portion 46A of the neck portion 20A, and which defines the receptor 38A (operatively comparable to the receptor 38, 38'). Further, the proximal sleeve member 44A is slidably received about the inner sleeve 58 such that the inner sleeve 58 is removable from the sleeve member 44 subsequent to implantation. In order for the distal stem portion 28A to releasably engage the proximal stem portion 24A, the upper end portion 36A of the portion 28A is provided with a protruding member 34A (operatively comparable to the member 34, 34') for being releasably received in the receptor 38A. It will also be noted that the protruding member 34A can be provided with a further threaded receptor 45A to facilitate removal of the distal stem portion 28A once the neck portion 20A and the inner sleeve 58 have been removed from the sleeve member 44A.

In light of the above, it will be appreciated that the present invention provides a femoral component with great advantages over the prior art. For example, the femoral component 10 allows the proximal and distal stem portions to be separately sized such that the stem closely engages the femur along the entire length of the stem. This reduces the possibility of post-implant movement of the femoral component which might result in disruption of the bone ingrowth process or result in post-implant pain to the recipient of the component. Further, should it become necessary to remove the stem, the neck portion and can be removed to provide access to the interior of the proximal sleeve such that cutting tools can be used to cut away the proximal sleeve, thereby facilitating its removal.

While a preferred embodiment has been shown and described, it will be understood that there is no intent to limit the invention to such disclosure, but rather it is intended to cover all modifications and alternate constructions falling within the spirit and scope of the invention as defined in the appended claims.

I claim:

1. A femoral component for a hip prosthesis, said hip prosthesis including an acetabular component provided with a cavity defining an acetabulum, said femoral component being for implantation into a femur, said femur defining a proximal portion and a medullary canal, said femoral component comprising:
    a neck portion defining an outboard end and defining a lower portion;
    a head portion mounted on said outboard end of said neck portion for being rotatably received by said cavity of said acetabular component; and
    a femoral stem including a proximal stem portion for being implanted in said proximal portion of said femur and a distal stem portion for being closely received by said medullary canal of said femur, said stem portion including an inner sleeve extending downwardly from said lower portion of said neck portion and a proximal sleeve for being closely received about said inner sleeve, said proximal sleeve defining a peripheral surface, said inner sleeve defining a receptor, said distal stem portion defining an upper end carrying a protruding member for being releasably received in said receptor of said inner sleeve, whereby said distal stem portion releasably engages said proximal stem portion.

2. The femoral component of claim 1 wherein said peripheral surface defines a porous surface portion for receiving bone ingrowth from said femur.

3. The femoral component of claim 1 wherein said protruding member defines an upper end provided with a further receptor for threadably receiving an extraction tool to facilitate removal of said distal stem portion from said femur.

4. A femoral component for a hip prosthesis, said hip prosthesis including an acetabular component provided with a cavity defining acetabulum, said femoral component being for implantation into a femur, said femur defining a proximal portion and a medullary canal, said femoral component comprising:
    a neck portion defining an outboard end and defining a lower portion;
    a head portion mounted on said outboard end of said neck portion for being rotatably received by said cavity of said acetabular component; and
    a femoral stem including a proximal stem portion for being implanted in said proximal portion of said femur and a distal stem portion for being closely received by said medullary canal of said femur, said proximal stem portion including a protruding member extending downwardly from said lower portion of said neck portion and a proximal sleeve for being closely received by said protruding member, said proximal sleeve defining a peripheral surface, said protruding member defining a free end portion extending beyond said proximal sleeve as said sleeve is received on said protruding member, said protruding member defining a morse cone and said sleeve defining tapered interior sidewalls for closely engaging said morse cone, said distal stem portion having an upper end provided with a receptor defining tapered sidewalls for closely receiving said free end portion of said protruding member, whereby said proximal stem portion releasably engages said distal stem portion.

5. The femoral component of claim 4 wherein said receptor of said distal portion defines a bottom portion provided with a further receptor for threadably engaging an extraction tool to facilitate removal of said distal stem portion from said femur.

6. The femoral component of claim 4 wherein said peripheral surface defines a porous surface portion for receiving bone ingrowth from said femur.

7. A femoral component for a hip prosthesis, said hip prosthesis including an acetabular component provided with a cavity so as to define an acetabulum, said femoral component for being implanted into a human femur, said femur defining a proximal portion and a medullary canal, said femoral component comprising:
    a neck portion defining an outboard end and defining a lower portion;
    a head portion for being releasably mounted on said outboard end of said neck portion and for being rotatably received by said cavity; and
    a femoral stem including a proximal stem portion for being implanted in said proximal portion of said femur and a distal stem portion for being closely received in said medullary canal of said femur, said proximal stem portion including a protruding member joined with and extending downwardly from said lower portion of said neck portion, said protruding member defining a morse cone having a free end portion, said proximal stem portion further including a proximal sleeve defining tapered interior walls closely engaging said protruding member, said sleeve defining a peripheral surface for engaging said proximal portion of said femur, said distal stem portion having an upper end provided with a receptor defining tapered interior sidewalls for closely receiving said free end portion of said protruding member whereby said distal stem portion releasably engages said proximal stem portion.

8. The femoral component of claim 7 wherein said peripheral surface defines a porous surface portion for receiving bone ingrowth from said femur.

9. The femoral component of claim 7 wherein said receptor of said distal portion defines a bottom portion provided with a further receptor for threadably engaging an extraction tool to facilitate removal of said distal stem portion from said femur.

10. A femoral component for a hip prosthesis, said hip prosthesis including an acetabular component provided with a cavity defining an acetabulum, said femoral component being for implantation into a femur, said femur defining a proximal portion and a medullary canal, said femoral component comprising:

a neck portion defining an outboard end and defining a lower portion;

a head portion mounted on said outboard end of said neck portion for being rotatably received by said cavity of said acetabular component; and a femoral stem including a proximal stem portion for being implanted in said proximal portion of said femur and a distal stem portion for being closely received by said medullary canal of said femur, said proximal stem portion defining an upper end for engagng said lower portion of said neck portion, a lower end and a peripheral surface, said peripheral surface defining a porous portion for receiving bone ingrowth from said femur, said lower end of said proximal stem portion carrying a protruding member defining a morse cone, said distal stem portion having an upper end provided with a receptor defining tapered sidewalls for closely receiving said morse cone of said proximal stem portion, whereby said proximal stem portion releasably engages said distal stem portion.

* * * * *